United States Patent [19]

Furuta et al.

[11] 4,031,746

[45] June 28, 1977

[54] AUTOMATIC TENSILE TEST APPARATUS

[75] Inventors: Isao Furuta, Suzuka; Shinsuke Iwamoto, Kyoto; Hironari Kuga, Muko; Yoshishige Chikatsu, Yokkaichi, all of Japan

[73] Assignees: Japan Synthetic Rubber Co., Ltd., Tokyo; Iwamoto Seisakusho Company Limited, Kyoto, both of Japan

[22] Filed: Apr. 29, 1976

[21] Appl. No.: 681,758

[30] Foreign Application Priority Data

Aug. 26, 1975 Japan .............................. 50-103351

[52] U.S. Cl. .................................................. 73/95
[51] Int. Cl.² ......................................... G01N 3/08
[58] Field of Search ........................... 73/95, 89, 90

[56] References Cited

UNITED STATES PATENTS 3,826,902   7/1974   Claxton et al. ..................... 73/95 X
3,926,042   12/1975  More et al. ......................... 73/95 X

*Primary Examiner*—Jerry W. Myracle
*Attorney, Agent, or Firm*—Toren, McGeady and Stanger

[57] ABSTRACT

An automatic tensile test apparatus includes an output device which supplies an elongation data of the specimen to the data processor in cooperation with means to optically detect said elongation, means to electrically detect said tension of said specimen and supply it to the data processor, and a device which detects the break of said specimen. Said output device generates a signal for causing the elongation strain and the tensile stress to be loaded into the data processor so as to correspond to each other. The break detector provides a break signal to the output device and the tension detecting means.

10 Claims, 12 Drawing Figures

AUTOMATIC TENSILE TEST APPARATUS

This invention relates to automatic tensile test apparatus which has been designed for automatically handling the tensile tests of various samples of vulcanized rubber and associated tests.

The most important subject in the tensile tests of this sort lies in the method selected for detecting the exact values of stress-and strain-at-break at the effective part of a sample for reading out the elongation ratio and the corresponding tensile stress of the sample continuously.

As to well-known tension testers such as the so-called Instron type machine, the aforementioned values have to be manually read from stress-strain curve on the recorder-chart, whereupon the values of stress, strain, Young's modulus etc. are evaluated through a calculating operation, for which a considerable labor time used to be expended. Moreover, test results obtained by such a method always include artifical errors and lack in reliability.

This invention intends to provide automatic tensile test apparatus wherein strain or stress value at the elongation of a sample are continuously measured and recorded directly without any hand operation of calculating various values as in the prior-art tension testers, and wherein a strain and a strain-at-break of the sample are also measured and recorded automatically in the same way.

The apparatus of this invention can be attached to any existing tensile tester, for example, an Instron type or Schopper type tension tester, in a unitary form without making any alteration or further working. The apparatus of the invention comprises an output device which, in cooperation with means which optically detects the elongation of a sample, causes a data processor, including a microcomputer, to continuously load the elongation data. The output device has a read data command mechanism which, when digitizing and delivering the analog quantity of elongation of the sample obtained by the elongation strain detector, causes the data processor to load the digital output through one of the several passes prearrangible in correspondence with the magnitudes of such elongation. In addition, the apparatus of this invention comprises a device which detects the break of the sample in association with said elongational strain detector. The sample break detector can initiate a "hold" to be transmitted said signal outo output device and a tension detector in immediate response to break of the sample. The tension detector digitizes the tensile value of the sample and delivers it to the data processor, and it is also supplied with a zero tension-detecting function.

The elongation strain detector optically detects the elongation of the sample, and the tension detector is constructed so as to be immediately attachable to the existing tester, so that the applicability of the apparatus according to this invention is of a very wide range.

Further, the apparatus of this invention comprises an elongational strain detector which can detect with an excellent follow-up property and high precision the strain of samples such as natural and synthetic rubber exhibiting a large elongation and which can electrically measure the important break data of the sample with high reliability. The elongational strain detector is provided with the function of checking the runaway of a strain detecting sensor and automatically returning the sensor to its original position at the time of the break of the sample.

In order to accomplish the object, the apparatus of this invention is provided with a pair of optical sensors two boundary marking lines formed at an effective elongation or stretch pair of the sample and each of which can be constructed of two sets of light emitting elements and light receiving elements, with a mechanism which supplies their outputs respectively to individual servomotors through amplifiers so as to cause the sensors to follow up (in correspondence with respective moving directions of) the boundary marking lines, and with the device which serves to convert and elongation of the sample into an electric signal in response to the movements of the sensors and which can be constructed so as to deliver a digital output. The mechanism for preventing the runaway of the sensors at the break of the sample is constructed so as to automatically shift the servomotors to a low controlled level by a sample break detecting either signal, a test specimen, or a zero tension. As to the shift, the sensors can be reset to their original positions in synchronism with a zero signal from the zero tension detecting device.

The sample break-detecting device has an especially high break data "hold" property, thereby to effect the function of perfectly checking the data processor from executing any insignificant operation and also to allow the data processor to conduct a reasonable operation.

The output device installed on a stage succeeding to the elongational strain detector is under the control of the read data command device by which BCD signals equivalent to the elongation of the sample are read by the data processor in correspondence with the tension. Thus, the construction of the output device can be remarkably simplified, and the apparatus is suitable as tensile test means for samples of large elongational strains such as vulcanized rubber.

The elongational strain detector has a highly-efficient characteristic of automatically following up the marking lines conjointly with a reasonable arrangement of the boundary marking lines affixed to the sample, and besides it is excellent in the performance of sensing the break of the sample. To this end, the elongational strain detector is equipped with a pair of sensors which optically sense the two boundary marking lines affixed to the sample and each of which includes two sets of light emitting and light receiving elements, one set being arranged in a horizontal state and the other set in a vertical state. Such structure of the sensors gives the optimum results to the automatic follow-up for the marking lines and the capability of sensing the rupture of the sample.

This invention is characterized by applying at least a powdery light reflecting substance onto a sample in order to form on the sample of a required shape, boundary marking line portions to cooperate with optical sensors. Owing to this expedient, the boundary marking line portions of the sample achieve a reliable sensor response action.

Other objects and features of this invention than stated above will be more clearly understood from the following description taken with reference to preferred embodiments illustrated in the drawings, in which.

Figure 1:
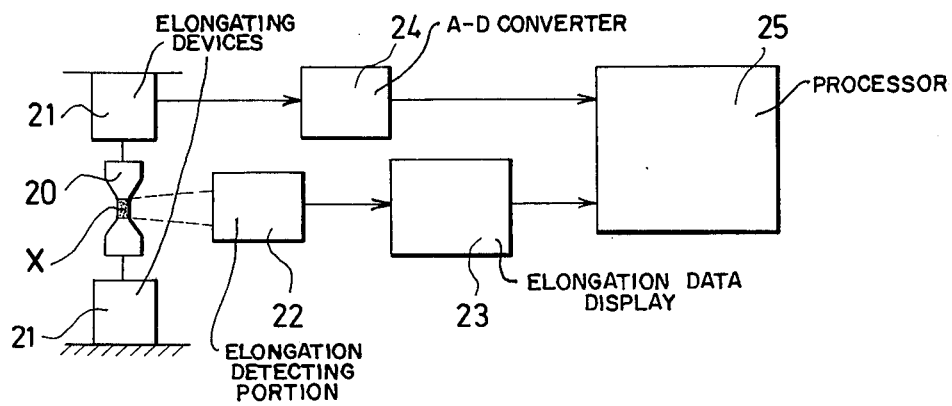
FIG. 1 is an overall block diagram of automatic tensile test apparatus of this invention.

FIG. 1 shows in a block diagram an example in which the automatic tensile test apparatus according to this invention is applied and in which the break stress value, the elongation ratio value etc. of a sample can be collectively subjected to data processings. Referring to the figure, numeral 20 designates a sample or tensile test piece of, for example, vulcanized rubber. Numeral 21 designates a device which elongates the test specimen 20. Numeral 22 indicates an elongational detecting portion, while numeral 23 represents an elongational data displaying and break detecting portion which cooperates with the detecting portion 22. The displaying and break detecting portion turns the elongation amount of the test specimen, inclusive of an exact elongation value at the break of the test specimen, into a digital signal continually and transmits a part thereof to a data processor 25 which comprises an electronic computer, a printer etc. On the other hand, a tensile load exerted on the test specimen 20 is continually given to the data processor 25 through the device 21 as well as an A–D converter 24. As the result, the processor 25 can prepare overall tensile test data including the rupture stress value, the elongation ratio value etc. of the test specimen 20.

Items to be minded most in the tensile test of this sort are the continuous detection of the elongation of the specimen and especially the security of a reliable elongation value at the break of the specimen. In this case, the specimen 20 of the illustrated dumbbell shape as stipulated in, for example, JIS or ASTM has a variety of sectional forms, and there need be comprised means which can reliably measure even the elongation of such specimen 20.

Figure 2:
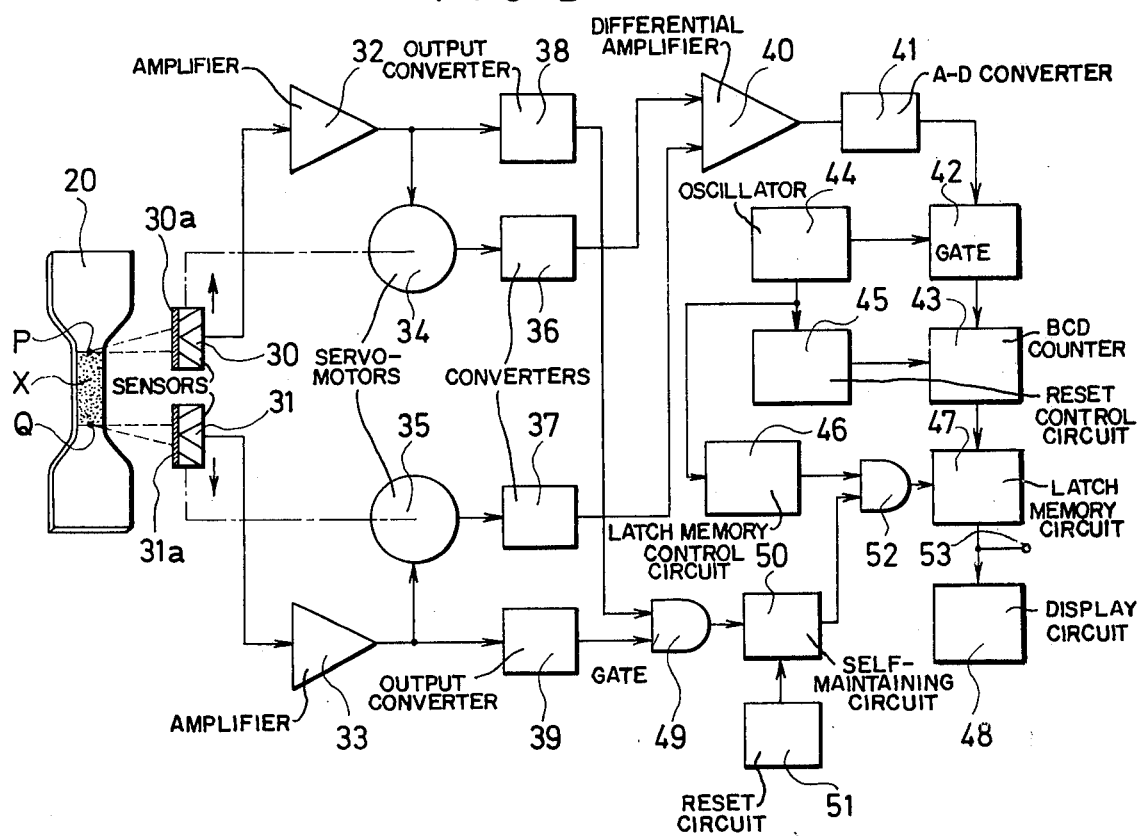
FIG. 2 is a block diagram showing an embodiment of the automatic tensile test apparatus according to this invention.

FIG. 2 shows in a block diagram an embodiment of the automatic tensile test apparatus according to this invention as can handle the tensile test of a specimen at high precision irrespective of the shape of the specimen. As illustrated in the figure, in this invention, a light reflecting substance X such as metal as finely pulverized is uniformly applied onto a surface of a dumbbell-shaped specimen 20 of, for example, vulcanized rubber directly without employing a dispersing agent, a solvent or the like, and the movements of both boundary marking lines P and Q defined by the light reflecting substance X and the specimen 20 are detected.

Numerals 30 and 31 designate sensors which serve to optically and individually detect the movements of both the boundary marking lines P and Q thus obtained, the movements being attendant upon the elongation of the specimen. The sensor 30(31) comprises a light emitting element and light receiving element with a convex lens which is excellent in directivity and which has a peak sensitive characteristic in the vicinity of an infrared spectrum in an invisible region, and a semitransparent plate 30a (31a) which is situated at the front surface of the element and which has the guard and optical filter function of preventing the sensor from sensing a level of usual illumination light in a laboratory or a factory at the time of the break of the specimen or the falling-off thereof. The sensor 30 (31) can have the angle between an emitting light flux and a receiving light flux adjusted, and it transmits an individual voltage signal of a high level or a low level to an amplifier 32 (33) at the succeeding stage in response to the receiption or unreception of reflected light from the marking line P (Q).

The specimen elongation detecting portion comprises, in addition to the pair of sensors 30 and 31, a well-known follow-up device which includes servomotors 34 and 35 for causing the sensors 30 and 31 to follow up the movements of the marking lines P and Q ascribable to the elongation of the specimen 20 in parallel with the movements, respectively. In the illustration, the sensor 30 is caused to follow up upwards by one follow-up means, while the sensor 31 is caused to follow up downwards by the other follow-up means. Shown at 36 and 37 are displacement — electric quantity converters such as potentiometers which are respectively associated with the servomotors 34 and 35, Outputs of the converters 36 and 37 are fed to a differential amplifier 40 which constitutes an elongation displaying portion. The elongation displaying portion consists of the differential amplifier 40; an A –D converter 41, a gate circuit 42, a binary-coded decimal counter 43, a latch memory circuit 47 and a display circuit 48, all of which are successively connected in cascade to the differential amplifier 40; a reference oscillator 44 for supplying clock pulses to the gate circuit 42; and a reset control circuit 45 and a latch memory control circuit 46 which control the counter 43 and the latch memory circuit 47 in cooperation with the oscillator 44. The displaying portion accordingly constructs a digital voltmeter or a frequency counter for digitally displaying a specimen elongation signal of the differential amplifier 40 continually.

The function of finally displaying the elongation value of the specimen 20 at the break thereof while the elongation of the specimen 20 is continually displaying on the display circuit 48 by the digital quantity, is based on a break detecting portion. The break detecting portion consists of output converter circuits 38, 39 which are respectively provided at stages succeeding to the amplifiers 32, 33 and which have a TTL level conversion and electric system filter function; an AND or NAND gate 49 which receives outputs of both the circuits 38, 39; a self-maintaining circuit 50 which is connected to the gate 49 and which is controlled by a reset circuit 51; and an AND gate 52 whose one input terminal is connected to the circuit 50 and which intervenes between the latch memory circuit 47 and its control circuit 46. Numeral 53 indicates an output terminal for the data processor. Since concrete examples of the above various constituent circuits are well known, the details are omitted here.

The example of the automatic tensile test apparatus according to this invention is made up of the construction described above. In response to the movements of the boundary marking lines P and Q as based on the initiation of the elongation of the specimen 20, therefore, the respective sensors 30 and 31 follow up at high precision in the directions of arrows in association with the corresponding follow-up devices. Thus, the amounts of movements of the sensors 30 and 31 are individually and continually applied to the differential amplifier 40 through the corresponding converters such as potentiometers 36 and 37. Here, the strain amount, i.e. elongation, of the specimen 20 is delivered to the A-D converter 41 at such precision that an error amount can be substantially neglected. The digitized elongations thus obtained are digitally displayed on the display circuit 48 in sequence under the action of the frequency counter. Also, they are entered into the data processor 25 through the terminal 53. It is accordingly possible to continually record the stress value, the elongation ratio value etc. of the specimen 20 under elongation by a recoder such as printer.

On the other hand, when the specimen 20 ruptures upon reaching the limit of the stress value thereof, the sensors 30 and 31 instantly change their detection signals from the previous high level to the low level. In consequence, both the signals are detected as rupture signals in the TTL level conversion and electric system filter circuits 38 and 39 through the amplifiers 32 and 33, respectively. Thus, the AND or NAND gate 49 is inverted to actuate the self-maintaining circuit 50, and to stop the signal transfer operation of the latch memory circuit 47 and cause this circuit to hold storage through the AND gate 52. Then, the elongation value at the rupture is stationarily held in the display circuit 48 as it is. The break elongation value is also entered into the data processor 25 as described above, and the break stress value and the elongation ratio value are recorded. By actuating the reset circuit 51 to reset the displaying portion, the tensile test of the next sample can be started again.

In the embodiment, the break detecting portion may satisfactorily have the function of holding the elongation displaying portion by the other inversion output of the elongation detecting portion owing to the output converting circuits 38 and 39. Accordingly, a variety of switching devices cooperating with, for example, a differentiation circuit can also be applied to the break detecting portion insofar as they do not spoil the detection response characteristic at the break of the specimen.

Comparative data obtained by the tensile test apparatus according to this invention and by prior-art Schopper type tensile test apparatus are listed below, $\bar{x}$ denoting the average value and $\sigma$ denoting the standard deviation. Samples supplied were of SBR No. 1500 (SBR No. 1500 produced by Nippon Gosei Gomu Kabushiki-Kaisha), and a compounding method, a kneading method etc. for the specimens conformed with ASTMD15.

The number of measurements $n$ was 132.

|  | Prior-art Apparatus | | Apparatus of Invention | |
| --- | --- | --- | --- | --- |
|  | $\bar{x}$ | $\sigma$ | $\bar{x}$ | $\sigma$ |
| 300 % tensile stress (Kg/cm²) Vulcanization time (min.) | | | | |
| (25) | 88.51 | 8.80 | 88.10 | 5.01 |
| (35) | 136.99 | 6.34 | 136.23 | 4.21 |
| (50) | 163.60 | 6.49 | 163.01 | 4.01 |
| Elongation (%) | | | | |
| (25) | 688.43 | 28.54 | 686.21 | 15.21 |
| (35) | 583.50 | 22.32 | 584.20 | 12.10 |
| (50) | 532.30 | 21.45 | 530.82 | 12.12 |

In the apparatus of the foregoing embodiment, the elongation displaying portion has the displaying operation stopped and is held directly by the output of the break detecting portion. However, in order to load the elongation strain and the tensile value of the specimen into the data processor in the manner corresponding with each other in the course of the elongation of the specimen and at the break thereof, the provision of an output device for the data processor is favorable as will be apparent from an embodiment to be stated below. It is also favorable in the tensile test apparatus of this sort to provide a break "hold" circuit at a stage succeeding to a break detector and to effectively control at least the data processor at the break of the specimen. The embodiment shown in FIG. 3 accedes to such requests.

Figure 3:
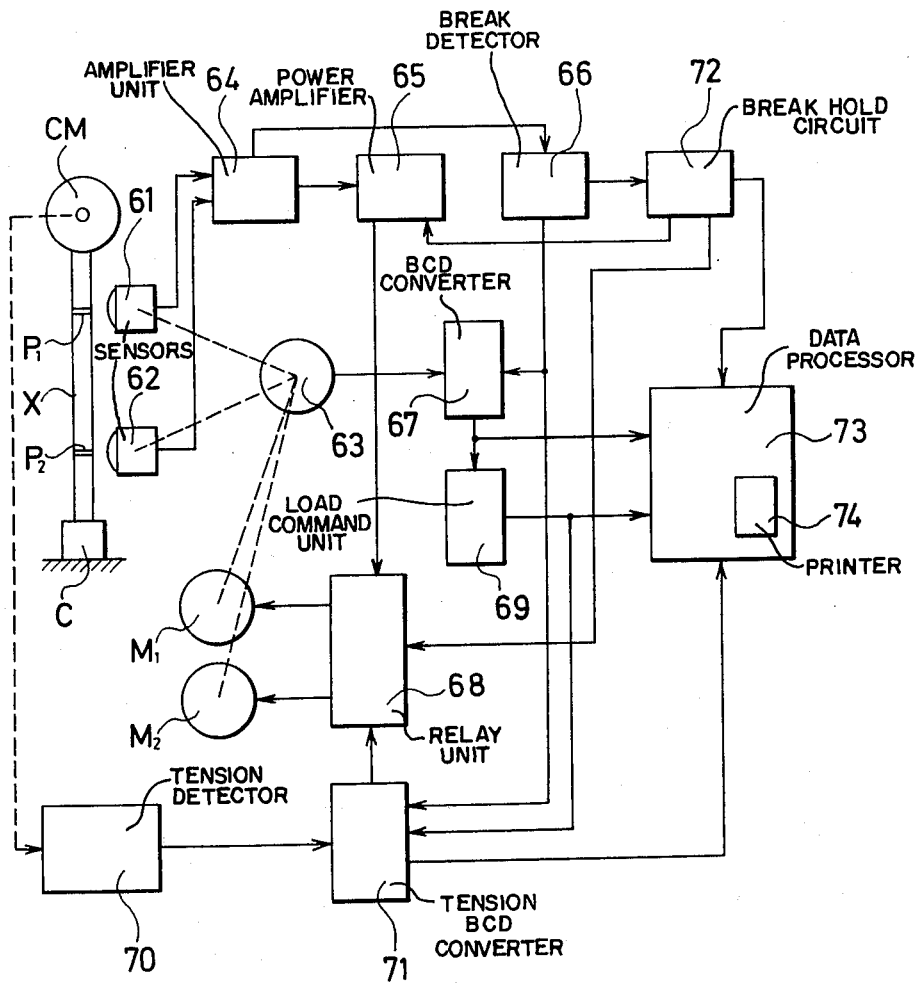
FIG. 3 is a block diagram of the automatic tensile test apparatus which is based on another preferred embodiment according to this invention.

In FIG. 3 which shows in a block diagram the preferred embodiment of the automatic tensile test apparatus according to this invention, a specimen X to be furnished for the tensile test is dumbbell-shaped in case of, for example, vulcanized rubber and has boundary marking line portions $P_1$ and $P_2$ at both ends of an effective elongation part thereof. Such specimen X is attached to an existing Schopper type tensile machine CM in a well-known aspect by using a chuck C of the machine. Numerals 61 and 62 designate upper and lower optical sensors which are arranged in parallel in a manner to confront the marking lines $P_1$ and $P_2$ of the specimen X, respectively. Both the sensors 61 and 62 may be known sensors for some kinds of the specimen X to be measured. However, as regards the specimen of vulcanized rubber or the like whose elongation strain is several times as large as the original state, it is the most suitable that each of the sensors 61 and 62 is composed of two sets of light emitting elements and light receiving elements. Although not shown, one set of the light emitting and light receiving elements is arranged horizontally so as to extend in the same direction as that of the marking line portion, and the other set is arranged vertically. Owing to the arrangement, the sensors 61 and 62 are enabled to have excellent pickup functions for the respective marking lines.

Means for causing the upper sensor 61 and the lower sensor 62 to follow up in correspondence with the moving directions of the respective marking lines $P_1$ and $P_2$ includes servomotors $M_1$ and $M_2$ and an interlocking mechanism 63 which are well known. The servomotors $M_1$ and $M_2$ individually drive the upper sensors 61 and the lower sensor 62 through the mechanism 63 in the follow-up manner, respectively.

While the procedure of forming the marking lines $P_1$ and $P_2$ differs variously in dependence on the kind of the specimen, it will now be exemplarily described of the specimen such as vulcanized rubber.

Figure 4:
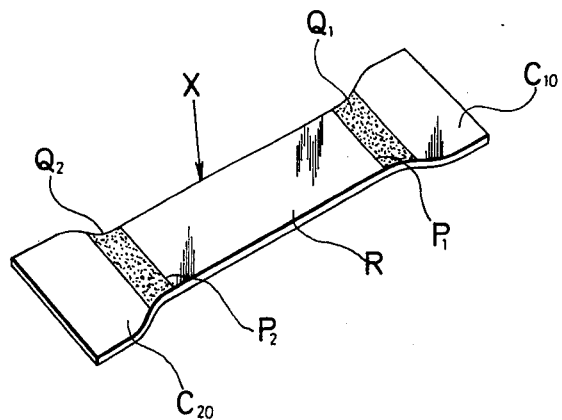
FIG. 4 is a conceptual perspective view of a sample which is suitable when applied to the apparatus of this invention.
Figure 5:
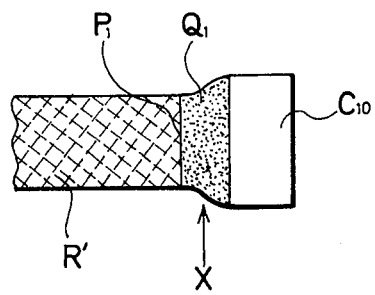
FIG. 5 is a partial plan view of the sample according to another embodiment.
Figure 6:
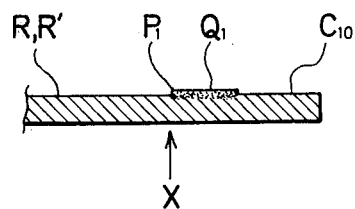
FIG. 6 is a view for elucidating an aspect of stretch of a boundary marking line portion of the sample.

As shown in FIG. 4, such specimen exhibiting a great elongation strain value is formed into the well-known dumbbell shape stipulated in JIS, ASTM etc. Boundary marking line portions $Q_1$ and $Q_2$ to be affixed to both ends of an effective elongation portion R of the specimen can be formed in such way that a light reflecting material made of a white fine powder metal such as aluminum fine powder is uniformly applied onto the pertinent portions. In applying the light reflecting substance, it is of course possible that the light reflecting substance is suspended and mixed into a material such as silicone oil having the optimum tenacity for the material of the test specimen and being rich in viscosity and ductility, thereby to obtain a pasty matter, and that the paste is suitably applied onto the pertinent portions. Regarding electrically nonconductive specimens exhibiting conspicuously large elongation strain values, for example, the specimen of vulcanized rubber, however, it has been verified rather preferable that as illustrated in FIG. 6, the boundary marking line portions $Q_1$ and $Q_2$ are formed by directly rubbing the light reflecting substance onto the pertinent portions by fingers or with a brush or the like. According to such aspect of application, the light reflecting substance is electrostatically stuck and applied onto the specimen surface. It is therefore possible to provide the most suitable boundary marking lines $P_1$ and $P_2$ for both the optical sensors 61 and 62 in spite of the stretches of both the boundary marking line portions in the elongating process of the specimen X. Where the ground of the specimen X is black, the above procedure suffices. On the other hand, where the ground is white, an appropriate light absorbing substance R' should preferably be suitably applied onto the other part than the boundary marking line portions $Q_1$ and $Q_2$ as illustrated in FIG. 5.

Further, good boundary marking lines $P_1$ and $P_2$ can be easily acquired in such way that, in forming the boundary marking line portions $Q_1$ and $Q_2$, tape pieces or the like are stuck onto parts adjacent to the portions $Q_1$ and $Q_2$ beforehand, whereupon the light reflecting substance is applied in accordance with the foregoing aspect.

While the embodiment has been explained of the specimen such as synthetic rubber exhibiting a marked elongation strain, it is applicable not only to such member but also to a member such as metal and alloy having a high ductility.

The specimen for the tensile test has the boundary marking line portions most suited for measuring the elongation strain of the specimen with the contact-free optical sensors or the like, and it makes it possible to handle the tensile test of this sort highly precisely. Especially, when the specimen is applied to the electrically nonconductive member such as synthetic rubber developing a large elongation strain, an excellent adhesive property and ductility owing to an electrostatic synergetic effect, so that boundary marking line portions capable of maintaining a good efficiency of reflecting light are easily secured.

Referring back to FIG. 3, the servo follow-up loop for the upper and lower sensors 61 and 62 comprises an amplifier unit 64 which amplifies the outputs of both the sensors 61 and 62 individually and feeds them back to the servomotors $M_1$ and $M_2$ respectively. A power amplifier 65 by which the sense signals of both the sensors 61 and 62 as delivered from the amplifier unit 64 are further amplified individually is connected to a relay unit 68 for controlling the operations of the servomotors $M_1$ and $M_2$. The servo follow-up loop drives the upper sensor 61 in the upward movement direction of the marking line $P_1$ and the lower sensor 62 in the downward movement direction of the marking line $P_2$ in response to the elongation of the specimen X owing to the tensile machine CM. The elongation strain of the specimen X is converted into an analog electric signal by the converter such as well-known potentiometer disposed in the interlocking mechanism 63, and is thereafter entered into a BCD (binary-coded decimal) converter 67 for digitizing the analog signal. An output of the BCD converter 67 is supplied into a data processor 73, including a microcomputer etc., through cooperation of the function of a load command unit 69.

When the specimen X breaks in the last stage of the elongation, the break is immediately detected by a break detector 66 through the amplifier unit 64. A break detection signal at that time is bestowed on the elongation strain-BCD converter 67 and a tension-BCD converter 71. The tension-BCD converter 71 is connected to a tension detector 70 detecting a tensile value corresponding to the elongation strain of the specimen X, and it digitizes the tensile value and bestows it on the data processor 73. Accordingly, the data processor 73 prints out the elongation strain, tensile value, stress, Young's modulus etc. of the specimen X through a printer 74.

When the break detector 66 operates, the elongation strain-BCD converter 67 and the tension-BCD converter 71 deliver a break elongation strain and a break tension value to the data processor 73, respectively. The break signal delivered from the break detector 66 is entered into a break "hold" circuit 72, a "hold" signal of which is supplied to the data processor 73 so as to deliver the various values at the break of the specimen from the printer 74. The hold signal is also applied to the power amplifier 65 and the relay unit 68. Thus, the servo follow-up device is stopped, and the sensors 61 and 62 are automatically reset to their original positions.

Figure 7:
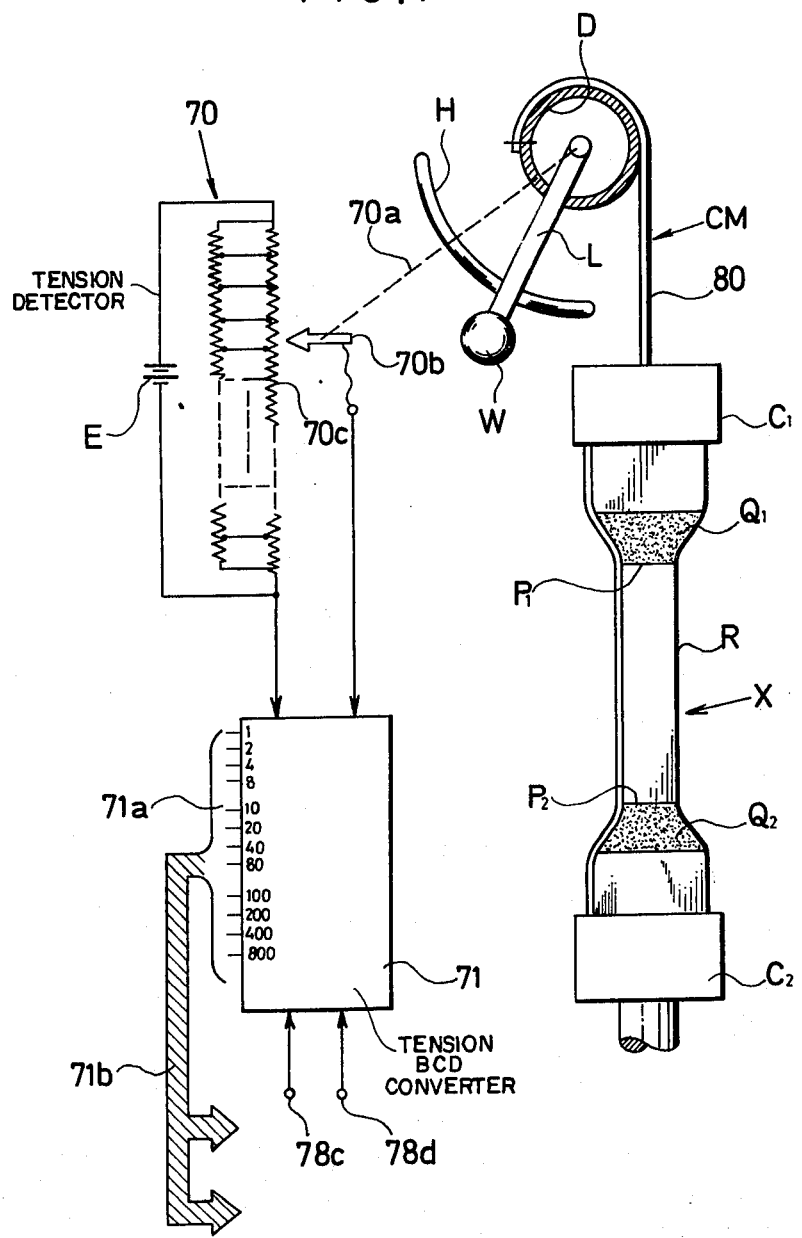
FIG. 7 is a view showing an example of a tension detector.

Shown in FIG. 7 is the specimen in the case where the tensile test apparatus indicated at 70 is attached to the existing Schopper type tensile machine CM. A chuck $C_1$ is fixed to one end of a steel belt 80 which is a part of a pendulum type tension detecting mechanism in the tensile machine CM of this sort. The other end of the belt 80 is fixed by being wound round a part of the circumference of a pulley D. When the specimen X is mounted between chucks $C_1$ and $C_2$ and a mechanical tensile force of uniform speed is applied to the chuck $C_2$, a balancing weight W of an arm L coupled to the pulley D moves. Then, an inclination angle of the weight W is read on a scale plate H, whereby the value of a tension exerted on the specimen X can be known. It is desirable that the tension detector 70 provided by this invention can be attached to such Schopper type tensile machine CM without performing any alteration or working.

To this end, in accordance with this invention, the tension detector 70 is associated by inserting coupling means of, e.g., a permanent magnet through a turning shaft of the pulley D or the arm L. This is conceptually illustrated by a broken line 70a in the figure. The device 70 consists of a potentiometer 70c for converting a tension into an electric signal, a rotary slide member 70b mounted by the means described above, and a d.c. power source E. Such potentiometer should desirably be as low in torque as possible so that the influence of a mechanical frictional resistance on a tensile value obtained in the tester CM may be almost negligible, and be satisfactory endurable even in repeated uses. Further, the potentiometer 70c of such type should desirably be equipped with function resistors so that the tensile value on the specimen X may be converted into the electrical analog signal at high precision and fidelity.

A d.c. voltage signal delivered from the tension detector 70 is digitized in the tension-BCD converter 71, and the digital signal is fed to the data processor 73 through output terminals 71a and an output route 71b of the converter. The BCD converter 71 has a control input terminal 78c which receives a preset pulse signal from the load command unit 69 for the elongation strain of the specimen X, and another control input terminal 78d which receives the break "hold" signal from the break detector 66. When the preset pulse signal is entered into the former terminal 78c, the tensile value in the increasing process is held for a moment at every such preset pulse signal corresponding to a predetermined set distortion factor owing to the elongation strain-BCD converter 67 as well as the load command unit 69. Under such proceeding of the operation, the tensile value is loaded into the data processor 73. Therefore, the elongation strain and the tensile value of the specimen as arbitrarily set are precisely put into a corresponding relationship. When the control input terminal 78d receives the break "hold" signal, the BCD converter 71 holds the break tension value of the specimen X and loads it into the data processor 73.

Figure 8:
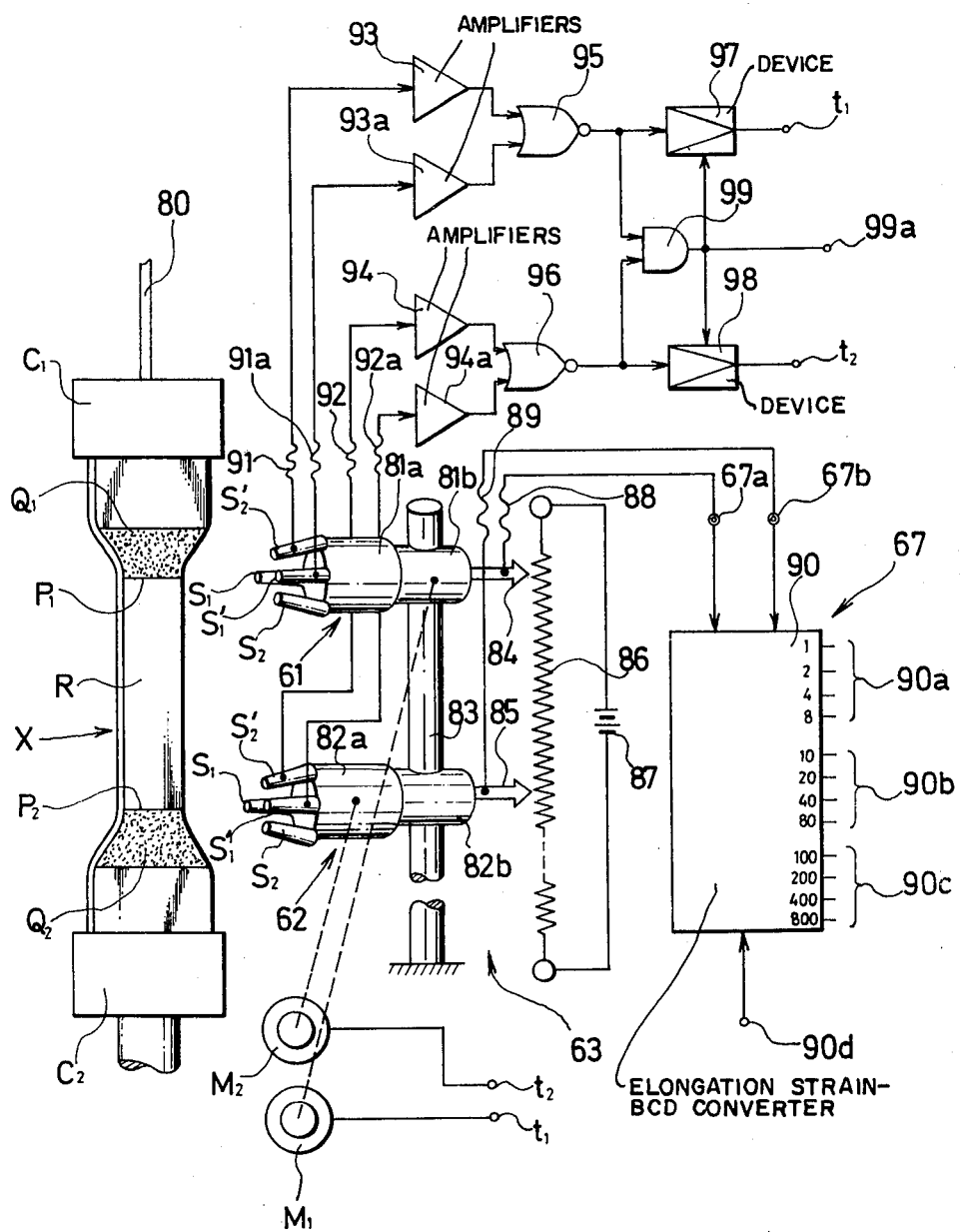
FIG. 8 is a conceptual constructional view showing an embodiment of an elongational strain detector.

FIG. 8 shows the details of the elongation strain detector.

Each of the pair of upper sensor 61 and lower sensor 62 has one set of a light emitting element $S_1$ and a light receiving element $S_1'$ which are disposed at an end part of a sensor body 81a (82a) horizontally and at a predetermined angle between them in a form or state as shown by way of example in the figure. The sensor 61 (62) also has another set of a light emitting element $S_2$ and a light receiving element $S_2'$ which are similarly disposed perpendicularly to a line joining both the elements $S_1$ and $S_1'$. The marking lines $P_1$ and $P_2$ of the specimen X are accordingly sensed in the follow-up manner by the respective two sets of light emitting and light receiving elements which are provided horizontally and vertically.

Numeral 83 indicates a sensor slide shaft, which is arranged in parallel to an elongation feed mechanism of the Schopper tensile machine or the like not shown. In addition, both the sensors 61 and 62 are slidably mounted on the slide shaft 83 through respective sensor bearing portions 81b and 82b. Numerals 84 and 85 denote slide members which are protrusively provided on the respective sensor bearing portions 81b and 82b, and which move in contact with a strain detecting potentiometer 86 connected to a variable constant voltage power sorce 87 in response to the follow-up movements of the sensors 61 and 62.

The sensors 61 and 62 should preferably be equipped with spline coupling bearings, such as ball slide bearings cooperating with the slide shaft 83, in the respective bearing portions 81b and 82b as turning preventing means for the slide shaft 83. Desirably, the angles of disposition of the light emitting and light receiving elements $S_1$, $S_2$ and $S_1'$, $S_2'$ are made symmetric angles which are determined from the distances between these elements and the plane of the specimen X as well as the spacings between the elements $S_1$ and $S_1'$ and between the elements $S_2$ and $S_2'$, and the elements are suitably fixed or provided adjustably at the end parts of the respective sensor bodies 81a and 82a. Although no illustration is made in the figure, it can be arbitrarily done that light emitting elements capable of projecting, for example, invisible infrared rays are applied as those $S_1$ and $S_2$ in order to check any evil effect of disturbance light rays and that convex lenses are individually attached to at least the fore end parts of the light emitting and light receiving elements so as to turn the sensing light rays of the elements into beams.

The slide members 84 and 85 are coupled with a BCD (binary-coded decimal) converter 90 through flexible wires 88 and 89, respectively. The BCD converter 90 further converts into a digital signal the signal having been obtained by electrically converting the operation strain of the effective elongation portion R of the specimen X by means of the potentiometer 86. 90a, 90b and 90c designate output terminal groups of the converter 90. The terminals associate the minimum measured amount of strain values with a data processor, including a microcomputer, a component of recording and displaying functions, etc., through a strain value output device which is appropriately settable although not shown. 90d designates an input terminal for the rupture signal of the specimen X. Upon reception of the input signal, the BCD converter 90 stops its operation.

The specimen X is attached to chucks $C_1$ and $C_2$ of the Schopper tensile machine or the like, the resultant structure is connected through a rope 80 to a tension detecting mechanism for the specimen X, and the chuck $C_2$ is pulled downwards. Then, boundary marking lines $P_1$ and $P_2$ formed at both ends of the effective elongation portion R move upwards and downwards, respectively. The sensors 61 and 62 move upwards and downwards in response to the movements of the marking lines $P_1$ and $P_2$ by the operation of a well-known servo follow-up mechanism which includes servomotors $M_1$ and $M_2$ corresponding thereto, respectively. Here, in this invention, the horizontal and vertical light receiving elements $S_1'$ and $S_2'$ of the upper sensor 61 (lower sensor 62) have amplifiers 93a and 93 (94a and 94) connected thereto through flexible wires 91a and 91 (92a and 92), respectively. In addition, an individual NOR gate 95 (96) is provided at the output stage of the paired amplifiers 93 and 93a (94 and 94a). An output of the NOR gate 95 (96) is applied to an input terminal $t_1$ ($t_2$) of the servomotor $M_1$ ($M_2$) through a device 97 (98) including a feedback amplifier etc.

The servo follow-up loop has various favorable characteristics in cooperation with the upper and lower sensors 61 and 62 each having the two sets of light emitting and light receiving elements. If, for example, the ground of the specimen X is close to black, the light receiving elements $S_1'$ and $S_2'$ feed signals L indicative of low region values to the NOR gate 95 (96) through the respective amplifiers 93a and 93 (94a and 94) as to both the end parts of the effective elongation portion R. The NOR gate 95 (96) provides a signal H corresponding to a follow-up output only when both the inputs are the signals L. On the other hand, where reflected light is to be received from the marking lines $P_1$ and $P_2$, the amplifiers 93 - 94a deliver signals H indicative of high region values in a manner converse to the above. When the signals H are applied to all the input terminals of the NOR gates 95 and 96, the NOR gates provide signals L. The output signal H of the NOR gate 95 is suitably amplified in the device 97 including the feedback amplifier etc., and is entered into one servomotor $M_1$ through the terminal $t_1$. Then, the servomotor $M_1$ drives the sensor 61 upwards as viewed in the figure in the follow-up manner through an interlocking mechanism shown by a broken line. Likewise, the output signal H of the other NOR gate 96 is amplified by the other device 98 having the same function as the device 97 and is entered into the other servomotor $M_2$ through the terminal $t_2$. Since the servomotor $M_2$ is so constructed as to have the opposite polarity to that of the motor $M_1$, it drives the lower sensor 62 downwards in the follow-up manner by the signal H of the NOR gate 96.

The follow-up detection mechanism for the marking lines $P_1$ and $P_2$ as described above has, besides the advantage of subjecting the paired upper and lower optical sensors 61 and 62 to the follow-up controls by the respective independent servo loops, an especially great advantage owing to the structure of the sensors 61 and 62. More specifically, each sensor 61 (62) is equipped with the two sets of light emitting elements $S_1$, $S_2$ & light receiving elements $S_1'$, $S_2'$, the respective sets being disposed horizontally and vertically. Both the sensors 61 and 62 therefore effect good follow-up sensing functions even in case where the quantity of reflected light from the specimen X interrupts or changes in the elongating process of the sample X on account of shakings attributed to the torsion, bending etc. of the specimen itself, and a case where a variety of unfavorable influences such as a change in the width of the specimen X and some lowering in the reflection efficiency of the boundary marking line portions $Q_1$ and $Q_2$ are exerted. Usually, in order to enhance the sensing function of the sensor of the specified sort, there are adopted such expedients as intensifying the quantity of light of the light emitting element and raising the sensitivity of the amplifier connected to the light receiving element. With such expedients, however, it is feared that a value equivalent to the white level of the specimen is sensed in a region of the brightness of the interior of a room. Besides, slight luster or gloss on the surface of the specimen tends to be sensed as the white level.

According to the sensor structure of this invention, such disadvantages can be fully eliminated. In case of, for example, the specimen X of the black ground, a marking line follow-up operation which is sufficiently satisfactory in practical use has been enabled. Such high reliability of the marking line follow-up operation secures a more sufficient automatic tracking between the marking lines conjointly with the reasonable arrayal of the applied marking lines because, in the elongating process in which the specimen X of this sort gives rise to an extremely large elongation strain, the effective elongation portion R of the specimen X gradually loses its luster and the reflected light from this portion abruptly decreases accordingly.

In FIG. 8, numeral 99 designates an AND gate for detecting the break signal of the specimen X, and symbol 99a an output terminal thereof. When both the outputs of the NOR gates 95 and 96 are at the H level, the AND gate 99 provides an active H level. By this active H level, it is instantly detected that the specimen X has broken. The break signal delivered from the terminal 99a is applied to the devices 97 and 98. Thus, the amplifiers in both the devices 97 and 98 are respectively switched to a state of floating sides including only feedback resistances, by means of relays contained or separately provided. As the result, the servomotors $M_1$ and $M_2$ are stopped by low amplification gains from the terminals $t_1$ and $t_2$. According to the actuating mechanism described above, the runaway of the sensors 61 and 62 can be perfectly checked at the break of the specimen X. By way of example, there can be reliably eliminated the fear that the sensor 61 or 62 will collide against the chuck $C_1$ or $C_2$ of the tensile machine to be destroyed.

The break signal delivered from the AND gate 99 is also applied to the BCD converter 90 through the terminal 90d and it immediately holds the output signal thereof. Then, the converter 90 bestows the break strain of the specimen X on the data processor 73 through the output terminal groups 90a – 90c.

In the tensile test apparatus of this sort, the tests are successively performed in such way that a specimen having broken is replaced with a new specimen. It is therefore preferably to promptly return both the sensors 61 and 62 to predetermined original positions after the break of the specimen X and to make preparations for the next strain measurement. Such automatic resetting mechanism for the sensors is necessary, not only for rendering the measuring manipulation convenient and efficient, but also for causing the apparatus to maintain a predetermined stable control function while the mixing of a human error etc. into a prearranged strain measuring accuracy is excluded as far as possible in association with the function of the control loop for automatically stopping the sensors simultaneously with the break of the specimen X.

Figure 9:
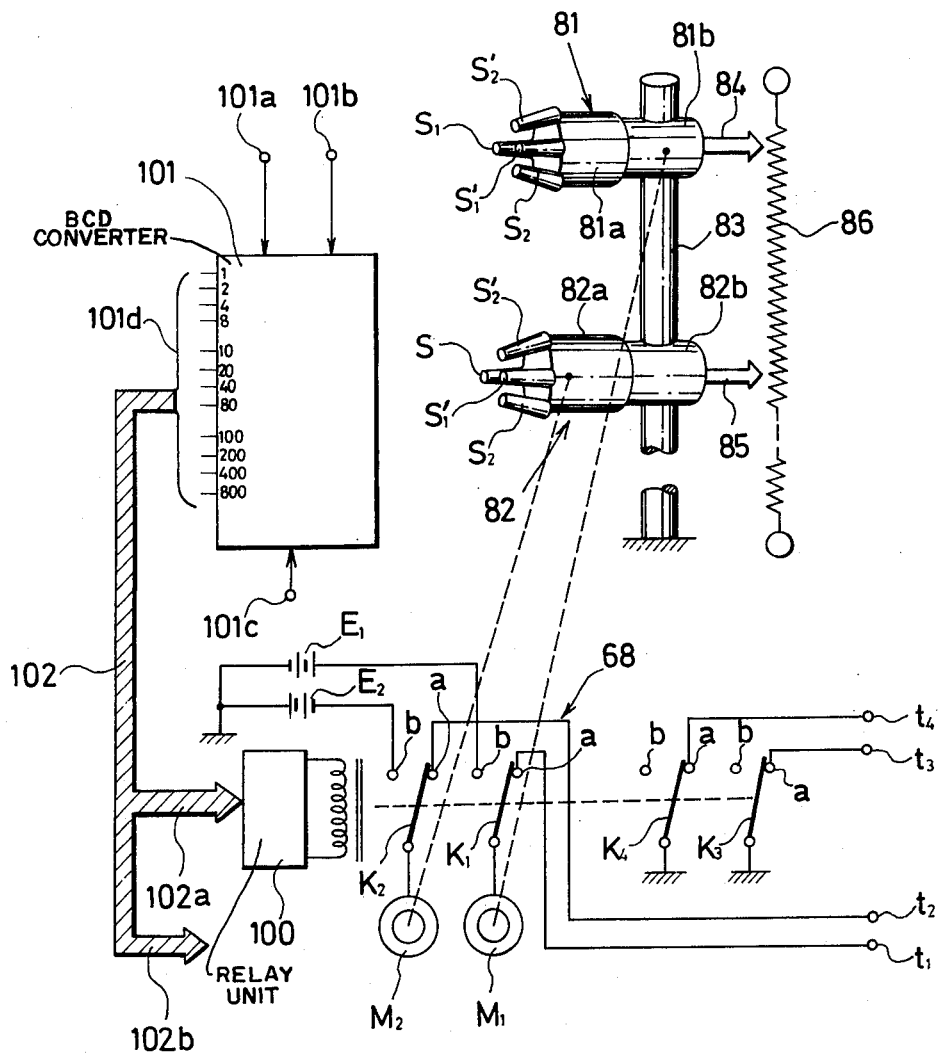
FIG. 9 is a circuit diagram showing an example of a mechanism for automatically resetting sensors.

FIG. 9 shows an example of such means for automatically resetting the sensors. Numeral 100 designates a relay unit, and numeral 101 a BCD converter which receives an input from tension — electric signal converting means not shown. The BCD converter 101 possesses input terminals for at least three kinds of different signals. Among the input terminals, one 101a is supplied with the signal from the tension — electric signal converting means. The electrical analog quantity of a tension as entered into the terminal 101a is converted in the converter into a digital quantity of a minimum tension value which can be preset, and the digital quantity is given through output terminals 101d to an output signal route 102 indicated by oblique lines. Another input terminal 101b receives an instant "hold" signal at a predetermined elongation strain to be stated later. Still another input terminal 101c can receive the rupture signal through the output terminal 99a from the AND gate 99 for detecting the break signal of the specimen X as shown in FIG. 8. Owing to the "hold" signal or signals impressed on the terminal 101b and/or the terminal 101c, the BCD converter 101 transmits not only a zero tension signal at the break of the specimen but also a value with a tensile value held in a time band equivalent to a control pulse width of the terminal 101b or 101c, to a data processor 73 through the output signal routes 102 and 102b.

A branch route 102a of the route 102 is exclusively for bestowing a drive input on the relay unit 100 on the basis of the zero tension signal. Thus, the relay unit 100 changes-over each of its responsive switches $K_1$ - $K_4$ from a contact a to another contact b. In response to the rupture of the specimen X, the servomotors $M_1$ and $M_2$ have been held in the stopped state through the terminals $t_1$, $t_2$ and the contacts a of the responding switches $K_1$, $K_2$ by the devices 97 and 98 in FIG. 8. Upon the operation of the change-over onto the side of the contacts $b$ of the responding switches $K_1$, $K_2$, however, the servomotors $M_1$ and $M_2$ are respectively connected to resetting drive power sources $E_1$ and $E_2$ prepared beforehand. The servomotors $M_1$ and $M_2$ accordingly drive the sensors 61 and 62 in the respective directions reverse to the elongating directions of the specimen so as to return them to the original positions fit for the specimen. The operation of stopping the resetting can be done in such way that microswitches or the like are appropriately provided in interlocking mechanisms between the servomotors $M_1$, $M_2$ and the sensors 61, 62 as indicated by broken lines and that the relay unit 100 is deenergized by the microswitches or the like. The contacts $K_3$ and $K_4$ serve for the detection processing of the break of the specimen.

When the tension and the tensile strain of the specimen X and their break values have been measured as set forth above, the apparatus automatically reverts to the original state. An operator can therefore automatically conduct the same strain measurements by setting new specimens to-be-measured on the chucks $C_1$ and $C_2$ in succession.

The elongation strain detector of this invention can subject various specimens, such as synthetic rubber exhibiting several times as large an elongation strain as an original length, to a strain measurement with an excellent follow-up characteristic and without any contact, and it is extraordinarily high in utility. The sensor follow-up mechanism responding to the movement of the boundary marking line of the specimen possesses a good stability and besides it can automatically reset the sensor to the original state in response to the break of the specimen, so that the test processing can be done highly efficiently with a high reliability bestowed on the strain measuring precision.

Figure 10:
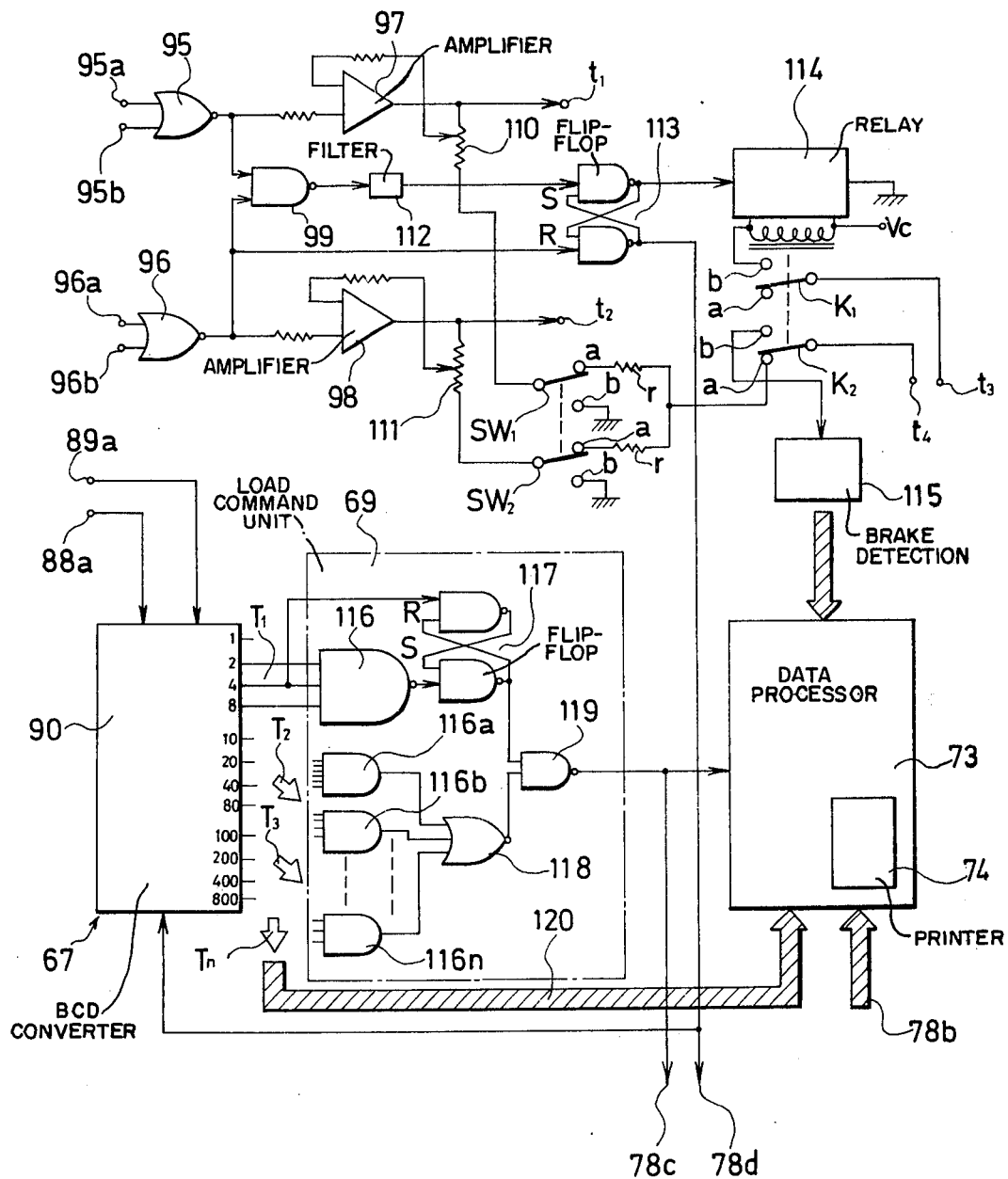
FIG. 10 is a circuit diagram showing an embodiment of a break detection and "hold" mechanism and an output device.

A detailed example of the break detecting mechanism as well as the load command unit for presetting the elongation strain is shown in FIG. 10. The mechanism for detecting the break of the specimen X need be insensitive to irregular electric signals such as fluctuations in the sense signal levels of the sensors 61, 62 for individually sensing and following up the boundary marking lines $P_1$ and $P_2$ affixed to the specimen and shakings attendant upon the elongation of the specimen, and need possess the function of immediately and reliably detecting only the break of the specimen. As explained with reference to FIG. 8, the two sets of light emitting elements and light receiving elements provided on each of the upper sensor 61 and the lower sensor 62 are disposed in a manner that the mounting positions on the respective sensor bodies can be adjusted, so as to be endowed with the optimum marking line follow-up characteristic. Two amplifiers 93 and 93a provided in an amplifier unit 64 are individually connected to the two light receiving elements arranged horizontally and vertically, of the upper sensor 61 for sensing a light reflection signal of the marking line $P_1$. Outputs of the respective amplifiers are applied to input terminals 95a and 95b of the NOR gate 95. Likewise, outputs of other two amplifiers 94 and 94a installed in the amplifier device 64 in order to amplify outputs of the two light receiving elements of the lower sensor 62 are respectively applied to input terminals 96a and 96b of another NOR gate 96. Outputs of feedback power amplifiers 97 and 98 which are connected in cascade to the NOR gates 95 and 96 are supplied to the relay unit 68 in order to bestow the driving outputs on the servomotors $M_1$ and $M_2$ through output terminals $t_1$ and $t_2$, respectively. Here, the amplifiers 97 and 98 constitute the power amplifier 65 shown by a block in FIG. 3. Numerals 110 and 111 indicate potentiometers for setting the gains of the amplifiers 97 and 98, respectively.

The break detector 66 shown in FIG. 3 has a NAND gate 99 which receives the outputs of the two NOR gates 95 and 96. The NAND gate 99 can provide an active output only when both the NOR gates 95 and 96 deliver the level H of a high region. According to such break detecting mechanism, the fear of an erroneous operation detecting that the specimen has broken is perfectly avoidable under the state under which, in the elongating process of the specimen X before the break thereof, the output signals of the NOR gates 95 and 96 repeat the level H of the high region or the level L of a low region or irregular shifts between both the levels. That is, although both the outputs of the NOR gates 95 and 96 in the elongating process of the specimen X present the low region level L for a moment in some cases, the existing period of time is shorter than that in the case of the break of the specimen, and hence, such situation is insufficient for inverting the NAND gate 99 to the active state. The rupture detection signal of the NAND gate 99 can accordingly offer a good and high signal-to-noise ratio even when the shaking of the specimen X, the allowed disorder of the servo follow-up mechanism, etc. are taken into consideration. Desirably, however, a filter circuit 112 is further provided at the output stage of the NAND gate 99. The filter circuit 12 has fixed or adjustable delay means for making the break detecting function satisfactory in adaptation to the material of the specimen X. As stated above, the break detector 66 has merely the construction cooperating with parts (NOR gates 95 and 96) of the servo follow-up loops of the sensors 61 and 62 and does not require any further means for detecting the break of the specimen. The apparatus can therefore be made simple in construction and low in cost.

The break "hold" circuit 72 installed at the stage succeeding to the break detector 66 consists of two stages of break signal holding means. One of them is an RS flip-flop circuit 113, and the other is constructed of a relay 114. The RS flip-flop circuit 113 has an S side terminal for "set" connected to the output end of the filter circuit 112 and an R side terminal for "reset" connected to the output end of the NOR gate 96. One of outputs of the RS flip-flop circuit 113 is applied to the relay 114, while the other output is supplied to the control input terminal 71d of the tension-BCD converter 71 shown in FIG. 7. The "reset" of the RS flip-flop 113 is performed by the first light reflection signal at the time when the specimen X having broken is replaced with a new specimen. The relay 114 is reset by the relay unit 68 which receives the zero tension signal having been detected by the tension-BCD converter 71. More specifically, when the relay 114 is energized upon receiving the break signal, a responding switch $K_1$ for self-holding thereof changes-over from a contact $a$ to a contact $b$ and holds the energization of the relay 114 in cooperation with a terminal $t_3$ and the relay unit 68 provided in the servo follow-up mechanism. Another responding switch $K_2$ also changes-over from a contact $a$ to a contact $b$, so that a break detection chatterfree circuit 115 is actuated through the relay unit 68 as well as a terminal $t_4$. The circuit 115 provides a command signal by which the break elongation strain attendant upon the break of the specimen, the tensile value, the stress, the Young's modulus etc. are loaded into the data processor 73. As regards the self-holding of the relay 114, when the realy unit 68 is energized upon receiving the zero tension signal of the tension-BCD converter 71, the holding circuit is opened through the terminal $t_3$ as well as the responding switch $K_1$.

Where the "hold" circuit 72 for the break detection signal is constructed of the RS flip-flop 113 and the relay 114 as described above, unless the relay 114 is reset by the zero tension detection signal the "hold" circuit 72 cannot be operated again by any signal other than the true break detection signal. In other words, when the "hold" circuit 72 receives the break detection signal delivered from the break detector 66, it holds the detection state thenceforth. Accordingly, a disturbance signal which arises thereafter due to any factor, for example, the intermission of irregular reflection of light at the removal of a broken piece after the break of the specimen or by the fingers of the operator or a transient time in the initial stage of the sensor follow-up for a new specimen is not sensed by the break detector 66. The chatter-free circuit 115 for bestowing the command signal of the break detector on the data processor 73 possesses also the function of a malfunction of the responding switch $K_2$ of the relay 114 due to chattering.

The input terminals 67a and 67b of the elongation strain-BCD converter 67 are connected to the potentiometer provided in the servo interlocking mechanisms 63 in FIG. 8. The BCD converter 67 loads the elongation strain of the specimen X into the data processor 73 in interlocking with the load command unit 69 provided at the next stage. The principal function of the load command unit 69 is to make control so that only an effective strain corresponding to the elongation of the specimen may be accurately loaded into the data processor when the digital elongation strain owing to the BCD converter 67 is applied to the data processor 73 through an output route 120. The BCD converter 67 digital-converts the elongation strain faithfully by a well-known aspect of operation and delivers the digital elongation strain to the data processor 73. The converter 67 itself, however, does not have the function of checking two or more pulses which arise in a strain of an identical stage for such cause as a slight disorder in the automatic servo follow-up mechanism for the sensors as constitutes the specimen strain measuring system. The load command unit 69 effects control so as to check the occurrence of such situation well and to load a tensile value corresponding to an elongation strain value into the data processor 73 through an output route 78b.

The load command unit 69 has a NAND gate 116 and an RS flip-flop 117 which detect the generation of a pulse belonging to the least digit among digital strain signal pulses delivered from the BCD converter 67 (the negative logic output being exemplified). An S side terminal of the flip-flop 117 for "set" is connected to an output terminal of the NAND gate 116, and an R side terminal for "reset" is connected to a terminal of binary number "4" in least-digit output terminals $T_1$ of the BCD converter 67. Thus, the flip-flop 117 is reset by strain signal pulses of "4," $-5$," "6" and "7" including "4." It is accordingly checked from being reset, for example, in case where the output shifts from "1" to "2" and thereafter returns to "1" or due to such unfavorable output pulses as proceed up to "9" in sequence and thereafter return to "0," "1" and "2." The load command unit 69 is further equipped with AND gates 116a, 116b, ... and 116n which are respectively connected to terminal groups $T_2$, $T_3$, ... and $T_n$ in order to detect strain signal pulses such as "10," "20" etc. provided from upper digits. Outputs of the AND gates are entered into an OR gate 118, and further lead to a NAND gate 119 which receives outputs of the flip-flop 117 and the OR gate 118. A terminal 78c applies to the tension-BCD converter 71 the load command signal provided from the NAND gate 119. Such construction of the load command unit 69 need merely provide one AND gate for the increase of one digit. It is therefore greatly useful in comparison with a case where it is constructed of, e.g., many stages of comparators.

In FIG. 10, $SW_1$ and $SW_2$ denote manual interlocking change-over switches which are connected to the potentiometers 110 and 111 of the power amplifiers 97 and 98, respectively. Each of the switches constructs an automatic stop servo follow-up system for the sensor at the break when it is thrown onto the side of a contact a. On the other hand, when it is changed-over to the side of a contact b and earthed, the servo normal operation is established. Resistors r are connected to the contacts a of both the switches, and their common juncture is connected to the contact a of the responding switch $K_2$ of the relay 114. As shown in FIG. 9, the responding switch $K_2$ is connected through the terminal $t_4$ to the relay unit 68 which controls the operations of the servomotors $M_1$ and $M_2$. Accordingly, when the responding switch $K_2$ changes-over to the contact b side and the relay 114 holds the break detection signal of the specimen X, the amplifiers 97 and 98 are respectively maintained in the states in which only feedback resistances are involved. Thus, control is so made that the servomotors $M_1$ and $M_2$ are automatically stopped simultaneously with the break of the specimen and that the sensors 61 and 62 are automatically returned to the original positions by the energization of the relay unit 68 a previously described.

Figure 11:
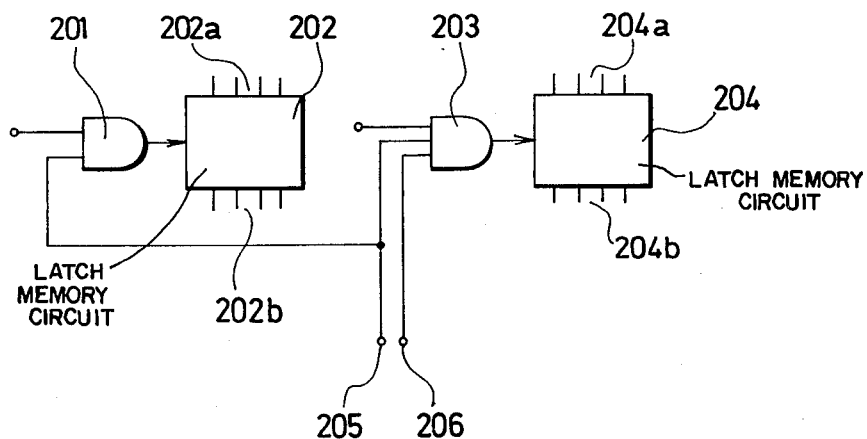
FIG. 11 is a diagram of an example of latch memory devices at the final output stages as are provided in BDC converters for an elongational strain and a tension.

FIG. 11 shows an example of a 4-bit latch memory device which is arranged in a final stage binary-coded decimal output system provided in the elongation strain-BCD converter 67 and the tension-BCD converter 71. In a latch memory circuit 202 (204), input terminals are indicated at 202a (204a) and output terminals at 202b (204b). The latch memory circuit 202 and an AND gate 201 which is connected to a clock terminal thereof belong to the elongation strain system, while a latch memory circuit 204 and another AND gate 203 belong to the tension system. In response to the reception of the load command signal at a terminal 205 and the reception of the beak detection signal at a terminal 206, the latch memory circuits 202 and 204 transmit the input signals to the output terminals 202b and 204b as they are, by the clock operations cooperating with the AND gates 201 and 203 respectively. Unless the signals are applied to both the control terminals 205 and 206, both the circuits 202 and 204 transmit latched outputs respectively.

Figure 12:
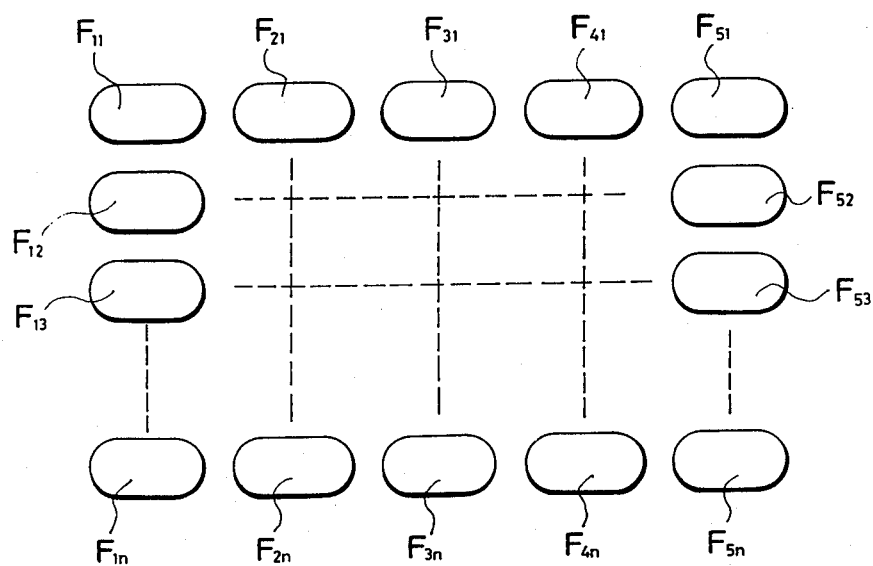
FIG. 12 is a diagram showing an example of a format by a printer.

Owing to the control system described above, the data processor 73 prints out the test values of the specimen X through the printer 74. FIG. 12 shows an example of a format printed out. In the figure, $F_{11}$ represents measured numerical values of a first specimen. $F_{12}$ and $F_{13}$ represent those of second and third specimens, respectively. $F_{1n}$ represents results of the summation mean value, weighted means value or the like for the individual measured values with respect to the number of test pieces. $F_{11}$, $F_{12}$ and $F_{13}$ include the ratio between the tensile value and the sectional area of the specimen, i.e., the stress value. Similarly, $F_{21}$ and $F_{31}$ indicate stress values which correspond to the tensile values of strains respectively set. A column of $F_{41}$ indicates rupture stresses to the break tensions of the respective specimens, while a column of $F_{51}$ indicates break strains as converted into percent values. $F_{52}$ and $F_{53}$ indicate such break strains of the second and third specimens, respectively. $F_{2n}$, $F_{3n}$, $F_{4n}$ and $F_{5n}$ are portions which indicate means values for the values of the respective columns.

In automatically disposing of the tensile test of the specified sort, this inventon realized to detect the elongation strain and tensile value of a specimen at high precision, and can also cause a data processor to calculate the stress value, the Young's modulus and the average values of various values with respect to the number of measured pieces from the detected values. In addition, the elongation strain and tensile value of the specimen at the break thereof can be reliably detected. Moreover, a highly reliable tensile test is ensured with the malfunction of the apparatus prevented. The invention is accordingly remarkable in practical value.

What is claimed is:

1. Automatic tensile test apparatus comprising a portion for detecting an elongational strain of a test specimen, said portion including sensors which optically detect movements in elongating directions of both boundary marking lines between said specimen and a light reflecting substance applied thereon and a follow-up device which cooperates with said sensors; means to detect a tension exerted on said specimen; means to detect break of said specimen in cooperation with the elongation strain detecting portion; and a data processor which continuously calculates and processes the detected elongation and tension of said specimen.

2. The automatic tensile test apparatus according to claim 1, comprising an elongation displaying portion which continuously and digitally displays an elongation of said specimen as based on output of said elongational strain detecting portion, and a break detecting portion which detects the break of said specimen on the basis of the output of said elongational strain detecting portion at the time of said break of said specimen, the displaying operation of said elongation displaying portion being stopped and held by an output of said break detecting portion.

3. The automatic tensile test apparatus according to claim 2 comprising a pair of upper and lower optical sensors which sense two boundary marking lines provided on said specimen, each sensor being constructed from two sets of light emitting elements and light receiving elements; a servomechanism which drives said sensors in a follow-up manner in corresponding with the respective moving directions of said boundary marking lines on the basis of outputs from said sensors; and a device which converts the elongation strain of said sample into an electric signal in response to the follow-up movements of both said sensors.

4. The automatic tensile test apparatus according to claim 3, wherein said servomechanism includes servomotors and resetting power sources and also comprising a sample break detector form a part of said servomechanisms, and a relay device which connects said servomotors to resetting power sources on the basis of a zero tension signal delivered in association with the resetting actuation of a tension detecting portion of said tensile tester.

5. The automatic tensile test apparatus according to claim 1, comprising an output device which supplies an elongation data of said specimen to said data processor in cooperatio with means to optically detect said elongation means to electrically detect said tension of said specimen and supply to it said data processor, and a device which detects the break of said specimen, said output device generating a signal for causing the elongation strain and the tensile stress to be loaded into said data processor so as to correspond to each other, the break detector providing a break signal to said output device and the tension detecting means.

6. The automatic tensile test apparatus according to claim 5, wherein said tension detecting means comprises a system which converts said tensile stress of said specimen into cooperation equivalent electrical analog quantity in association with said tension detecting portion of said tensile tester, and a tension-BCD converter which digitizes said analog quantity and supplies the digital value to said data processor, said BCD converter provides an output for a load command signal from both said output device and said break signal of said break detector.

7. The automatic tensile test apparatus according to claim 3, wherein said output device comprises a BCD converter which digitizes the elongation strain and enters the digital value into said data processor, and a load command device which has at an output stage of said converter a device resetting at a predetermined least digit of said elongational strain and an AND gate device for detecting output signals at upper digits and in which a NAND gate is connected to both these devices said tension detecting means and said data processor being controlled by the load command output.

8. The automatic tensile test apparatus according to claim 3, wherein said device which detects said break of said specimen comprises NOR gates which individually receive electrical outputs obtained by optically sensing the movements of said two marking lines affixed to said specimen and a NAND gate which receives outputs of both said NOR gates.

9. The automatic tensile test apparatus according to claim 8, wherein a break "hold" circuit is provided at a stage succeeding to the break detecting device, said circuit is constructed of a flip-flop which is set by an output of said NAND gate and a relay which holds the break signal in association with said flip-flop, and an output of said flip-flop is supplied to said output device and said tension detecting means to control them so as to provide the break values of said specimen to said data processor.

10. The automatic tensile test apparatus according to claim 8, wherein amplifiers for driving sensors by servomechanism to follow-up said marking lines of said specimen are switched to a feedback condition employing only feedback resistances in response to the energization of said relay so as to stop the servo follow-up mechanism simultaneously with the detection of said break of said specimen.

* * * * *